United States Patent [19]

Petruck et al.

[11] 4,409,407

[45] Oct. 11, 1983

[54] PROCESS FOR THE PREPARATION OF 1,3,5-TRICHLOROBENZENE

[75] Inventors: Gerd-Michael Petruck, Erkrath, Fed. Rep. of Germany; Paul R. Wambach, deceased, late of Leverkusen, Fed. Rep. of Germany, by Christa Wambach, heiress

[73] Assignee: Bayer Aktiengesellschaft, Leverkusen, Fed. Rep. of Germany

[21] Appl. No.: 408,347

[22] Filed: Aug. 16, 1982

[30] Foreign Application Priority Data

Sep. 2, 1981 [DE] Fed. Rep. of Germany ....... 3134726

[51] Int. Cl.$^3$ ............................................. C07C 17/24
[52] U.S. Cl. ................................................... 570/202
[58] Field of Search .......................................... 570/202

[56] References Cited

U.S. PATENT DOCUMENTS 2,866,829 12/1958 Woodruff .......................... 570/202

FOREIGN PATENT DOCUMENTS

C 947304 8/1956 Fed. Rep. of Germany .
2257343 1/1978 Fed. Rep. of Germany .

OTHER PUBLICATIONS

Chemistry Letters, No. 1, 1978, Tokio Y. Ono et al., "Low Temperature Conversion of Pentane with Aluminum Chloride-Metal Sulfate Mixtures", pp. 625 to 628.

*Primary Examiner*—Charles F. Warren
*Assistant Examiner*—Joseph A. Boska
*Attorney, Agent, or Firm*—Sprung, Horn, Kramer & Woods

[57] ABSTRACT

1,3,5-Trichlorobenzene is prepared by the isomerization of other trichlorobenzenes at an elevated temperature after the addition of aluminum trichloride and formic acid.

8 Claims, No Drawings

PROCESS FOR THE PREPARATION OF 1,3,5-TRICHLOROBENZENE

The invention relates to a process for the preparation of 1,3,5-trichlorobenzene by the isomerization of other trichlorobenzenes.

The preparation of 1,3,5-trichlorobenzene by the isomerization of other trichlorobenzenes in the presence of, for example, aluminum chloride and water (U.S. Pat. No. 2,866,829), in the presence of halides of aluminum and water or alcohols (German Patent Specification No. 947,304), in the presence of aluminum chloride and magnesium sulphate (Zh. Org. Khim. 1968, 1247) and in the presence of aluminum chloride and magnesium chloride (CA 63, 9770a) is known.

The disadvantage of these processes is that relatively large amounts of catalyst are employed in order to achieve the yields of 1,3,5-trichlorobenzenes which are given in the references, but which are not always satisfactory for industrial use. Apart from this, when the procedure of U.S. Pat. No. 2,866,329 was reworked, the yields of 1,3,5-trichlorobenzene given therein was not achieved (see the comparative experiment carried out in this context). In addition, only unsatisfactory yields of 1,3,5-trichlorobenzene are obtained when pure 1,2,4-trichlorobenzene is used as the starting compound. Thus, for example, according to Example 6 of German 947,304, only 14% of 1,3,5-trichlorobenzene is obtained using pure 1,2,4-trichlorobenzene as the starting compound.

A process for the preparation of 1,3,5-trichlorobenzene by the isomerization of other trichlorobenzenes or mixtures thereof at an elevated temperature has now been found, which is characterized in that the isomerization is carried out after the addition of from 0.05 to 0.5 mol of aluminum chloride per mol of trichlorobenzene employed, and from 0.9 to 1.5 mols of formic acid per mol of aluminum chloride, at temperatures of from 150° to 300° C.

1,2,4- or 1,2,3-Trichlorobenzene, or mixtures thereof, in particular, are employed as starting materials for the process according to the invention. The isomerization is preferably carried out with 1,2,4-trichlorobenzene.

The aluminum trichloride employed may be of industrial grade, but it is frequently more advantageous to employ freshly sublimed aluminum trichloride. The aluminum trichloride is preferably used in amounts of from 0.1 to 0.2 mol per mol of trichlorobenzene employed.

The formic acid, which is customarily used in the form of pure formic acid (approx. 95 to 100% strength by weight), is preferably employed in an amount of from 1.0 to 1.2 mols per mol of aluminum trichloride.

The reaction temperatures of the process according to the invention are preferably from 200° to 250° C.

The process according to the invention may be carried out both under normal pressure and under elevated pressure (up to 50 bar, preferably from 1 to 20 bar).

To carry out the process according to the invention, the formic acid and the aluminum trichloride are added to the trichlorobenzene which has initially been introduced, and the mixture in the reactor is warmed to the desired temperature in the absence of moisture. The reaction mixture is worked up by filtering it off from the catalyst, washing the residue neutral with water, and distilling the filtrate in the customary manner to isolate the pure 1,3,5-trichlorobenzene. The non- isomerized trichlorobenzenes, which are obtained, for example, as a distillation residue, can be recycled to the isomerization. By this measure, the yield of 1,3,5-trichlorobenzene can be further increased.

The process according to the invention can be carried out both discontinuously and continuously.

By means of the process according to the invention, 1,3,5-trichlorobenzene, is obtained in particularly good yields, only small amounts of catalyst being required.

1,3,5-Trichlorobenzene is a valuable intermediate product, and can be used, for example, for the preparation of dyestuffs and plant protection agents (see, for example, German Offenlegungsschrift No. 1,811,843, German Offenlegungsschrift No. 2,207,576 and German Offenlegungsschrift No. 2,149,923).

EXAMPLES 1 to 8

Examples 1 to 8 are listed in the table below. This table also gives the reaction conditions, the yields and the percentage composition of the crude product. The composition of the crude product was determined by gas chromatography.

Examples 6 to 8 represent comparative examples which show that the content of the desired 1,3,5-trichlorobenzene in the crude product is lower when the isomerization is not carried out according to the invention, using aluminum trichloride/formic acid.

To determine the yields of crude product, the catalyst was additionally extracted with chlorobenzene.

| Example | Mixture (g) | Catalyst | Temperature (°C.) | Pressure (bar) | Time (hours) | Dichlorobenzene | Trichlorobenzene isomers 1,3,5- | 1,2,4- | 1,2,3- | Tetrachlorobenzene | Yield (g) |
|---|---|---|---|---|---|---|---|---|---|---|---|
| 1 | 363 g of 1,2,4-trichlorobenzene | 40.0 g of AlCl$_3$ 15.2 g of HCOOH | 250 | 16 | 48 | 5.8 | 29.3 | 52.4 | 5.2 | 7.2 | 290 |
| 2 | 363 g of 1,2,4-trichlorobenzene | 40.0 g of AlCl$_3$ 15.1 g of HCOOH | 250 | 16 | 16 | 6.0 | 28.7 | 51.1 | 5.1 | 8.1 | 290 |
| 3 | 363 g of 1,2,4-trichlorobenzene | 53.0 g of AlCl$_3$ 20.2 g of HCOOH | 200–210 | 1 | 24 | 8.9 | 27.4 | 49.0 | 4.8 | 11.2 | 280 |
| 4 | 363 g of 1,2,4-trichlorobenzene | 27.0 g of AlCl$_3$ 9.7 g of HCOOH | 250 | 16 | 24 | 3.9 | 26.3 | 58.9 | 6.0 | 4.9 | 300 |
| 5 | 363 g of 1,2,4-trichlorobenzene | 133.0 g of AlCl$_3$ 50.6 g of HCOOH | 250 | 16 | 5 | 8.1 | 29.0 | 47.6 | 4.7 | 10.7 | 190 |
| 6 | 363 g of | 26.6 g of AlCl$_3$ | 250 | 6 | 24 | 5.1 | 27.4 | 55.6 | 5.7 | 6.2 | 301 |

-continued

| Example | Mixture (g) | Catalyst | Temperature (°C.) | Pressure (bar) | Time (hours) | Composition of the crude product (%) | | | | | Yield (g) |
|---|---|---|---|---|---|---|---|---|---|---|---|
| | | | | | | Dichlorobenzene | Trichlorobenzene isomers | | | Tetrachlorobenzene | |
| | | | | | | | 1,3,5- | 1,2,4- | 1,2,3- | | |
| 7* | 363 g of 1,2,4-trichlorobenzene | 9.9 g of HCOOH 133.0 g of AlCl$_3$ 30.0 g of MgSO$_4$ | 300 | 16 | 5 | 12.3 | 20.0 | 34.3 | — | 9.3 | 210 |
| 8** | 363 g of 1,2,4-trichlorobenzene | 85.1 g of AlCl$_3$ 15.7 g of MgCl$_2$ | 180 | 16 | 36 | 4.8 | 23.4 | 59.2 | 5.0 | 7.5 | 220 |
| 9*** | 332 g comprising 79% of 1,2,4- and 21% of 1,2,3-isomers | 60.0 g of AlCl$_3$ 8.1 g of H$_2$O | 209–211 | 1 | 24 | 3.6 | 11.5 | 72.8 | 6.8 | 5.3 | 270 |

*Comparative example: according to Yu. G. Erykalov et al., Zh. Org. Khim 1968, 1247
**Comparative example: according to Yu. G. Erykalov et al., CA 63, 9770a
***Comparative example: according to D. Woodruff, U.S. Pat. No. 2,866,829

What is claimed is:

1. In a process for the preparation of 1,3,5-trichlorobenzene by isomerization of at least one other trichlorobenzene at an elevated temperature in the presence of aluminum trichloride, the improvement wherein the isomerization is carried out in the presence of formic acid.

2. A process according to claim 1, wherein the process is carried out at a temperature of from 150° to 300° C. after addition of from 0.05 to 0.5 mol of aluminum trichloride per mol of trichlorobenzene to be isomerized and in the presence of 0.9 to 1.5 mols of formic acid per mol of aluminum trichloride.

3. A process according to claim 2, wherein the process is carried out in the presence of from 0.1 to 0.2 mol of aluminum trichloride per mol of trichlorobenzene.

4. A process according to claim 2, wherein the isomerization is carried out in the presence of from 1.0 to 1.2 mols of formic acid per mol of aluminum trichloride.

5. A process according to claim 1, wherein the process is carried out in the presence of pure formic acid.

6. A process according to claim 4, wherein the process is carried out in the presence of pure formic acid.

7. A process according to claim 1, wherein the process is carried out at a temperature of 150° to 300° C.

8. A process according to claim 2, wherein the process is carried out at a temperature of 200° to 250° C.

* * * * *